(12) United States Patent
Sen et al.

(10) Patent No.: US 12,381,638 B2
(45) Date of Patent: Aug. 5, 2025

(54) COMMUNICATION AND POWERING SYSTEM FOR AN IMPLANTED SMART DEVICE AND USES OF THE SAME

(71) Applicant: PURDUE RESEARCH FOUNDATION, West Lafayette, IN (US)

(72) Inventors: Shreyas Sen, West Lafayette, IN (US); Mayukh Nath, West Lafayette, IN (US); Arunashish Datta, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 435 days.

(21) Appl. No.: 18/062,487

(22) Filed: Dec. 6, 2022

(65) Prior Publication Data
US 2023/0179308 A1 Jun. 8, 2023

Related U.S. Application Data

(60) Provisional application No. 63/286,459, filed on Dec. 6, 2021.

(51) Int. Cl.
*H04B 13/00* (2006.01)
*H02J 50/12* (2016.01)
*A61N 1/372* (2006.01)

(52) U.S. Cl.
CPC ............ *H04B 13/005* (2013.01); *H02J 50/12* (2016.02); *A61N 1/37229* (2013.01)

(58) Field of Classification Search
CPC .... H04B 13/005; H02J 50/12; H02J 2310/23; A61N 1/37229; A61N 1/3787
See application file for complete search history.

(56) References Cited

U.S. PATENT DOCUMENTS

| | | | |
|---|---|---|---|
| 9,923,383 B2* | 3/2018 | Ritter | H02J 50/12 |
| 2015/0365138 A1* | 12/2015 | Miller | H04B 5/79 |
| | | | 307/104 |
| 2018/0321280 A1* | 11/2018 | Komiyama | H02J 50/80 |
| 2018/0337547 A1* | 11/2018 | Menegoli | H02J 50/70 |
| 2020/0365316 A1* | 11/2020 | Tikka | H01F 38/14 |

* cited by examiner

*Primary Examiner* — Ping Y Hsieh
(74) *Attorney, Agent, or Firm* — Edmonds & Cmaidalka, P.C.

(57) ABSTRACT

A wearable device comprising a transmitter coil having variable transmission resistance, a first transmission impedance, and a second transmission impedance; an implanted device, comprising a receiver coil having a variable reception resistance, a first reception impedance, and a second reception impedance; wherein the transmitter coil can wirelessly transmit information over a variable frequency to the receiver coil when the variable resistance of the transmitter coil is tuned to the variable resistance of the receiver coil, the transmitter coil is configured to the first transmission impedance, and the receiver coil is configured to the first reception impedance; wherein the transmitter coil can wirelessly transmit power to the receiver coil when the transmitter coil is configured to the second transmission impedance and the receiver coil is configured to the second reception impedance; and wherein the transmitter coil can wirelessly transmit to the receiver coil of the implanted device using a magnetoquasistatic field.

8 Claims, 7 Drawing Sheets

COMMUNICATION AND POWERING SYSTEM FOR AN IMPLANTED SMART DEVICE AND USES OF THE SAME

GOVERNMENT FUNDING

This invention was made with government support under ECCS 1944602 awarded by the National Science Foundation. The government has certain rights in the invention

BACKGROUND

Field

The present disclosure in general relates to wireless communication between wearable and implantable Body Area Network (BAN) devices. Particularly, the present disclosure demonstrates a low power wireless communication and powering of implantable devices.

Description of the Related Art

Remote communication between a controlling hub and a smart contact lens through traditional wireless body area network (WBAN) techniques operating in the radio frequency (RF) range, such as Bluetooth, is difficult—owing to the power consumption requirement of RF transceivers—making it hard to implement in a small form factor such as that of a contact lens. Therefore, there is a need for technologies that use lower power to operate in wearables.

SUMMARY

A system comprising a wearable device comprising a transmitter coil having a first transmission resistance and a second transmission resistance; an implanted device, comprising a receiver coil having a first reception resistance and a second reception resistance; wherein the transmitter coil of the wearable device can transmit information to the receiver coil of the implanted device when the transmitter coil of the wearable device has a first transmission resistance and the receiver coil of the implanted device has a first reception resistance; wherein the transmitter coil of the wearable device can transmit power to the receiver coil of the implanted device when the transmitter coil of the wearable device has a second transmission resistance and the receiver coil of the implanted device has a second reception resistance; and wherein the transmitter coil of the wearable device can transmit to the receiver coil of the implanted device using a magnetoquasistatic field.

A smart contact lens by application of resonant Magneto Quasistatic (MQS) Human Body Communication (HBC), featuring 1) low channel loss compared to capacitive HBC implantable devices due to negligible absorption in the tissue in the quasistatic frequency range. 2) Tunable operating frequency 3) Switch-ability between communication and powering mode by manipulating the transmitter resistance. 4) High impedance receiver coil termination for communication mode and impedance matched receiver termination for power mode. 5) Possible low path loss (~50 dB) for frequencies 1 kHz-1 MHz, as well as 1 MHZ-20 MHz leading to a low loss power efficient high data rate communication.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are, therefore, not to be considered limiting of its scope, for the disclosure may admit to other equally effective embodiments. It is emphasized that the figures are not necessarily to scale and certain features and certain views of the figures can be shown exaggerated in scale or in schematic for clarity and/or conciseness.

FIG. 1A shows an Electro Quasistatic HBC setup involving body tissue.

FIG. 1B shows incompatibility of an Electro Quasistatic HBC setup for wearables.

FIG. 1C shows a Magneto Quasistatic HBC setup involving body tissue.

FIG. 1D shows an example of a Magneto Quasistatic HBC wearable setup using a necklace and a pair of contact lenses.

FIG. 2A shows a basic circuit schematic for Magneto Quasistatic HBC without a capacitor.

FIG. 2B shows a basic circuit schematic for Magneto Quasistatic HBC with a capacitor.

FIG. 4A shows a transmitter design for the simulation the Resonant MQS communication.

FIG. 4B shows a receiver design for a simulation of the Resonant MQS communication.

FIG. 4C shows a comparison between a resonating and non-resonating transmitter cases, with both the receiver and transmitter coil consisting of only a single turn.

FIG. 4D shows a comparison between the voltage transfer cases between single turn and multi turn coils.

DETAILED DESCRIPTION

Figure 1A:
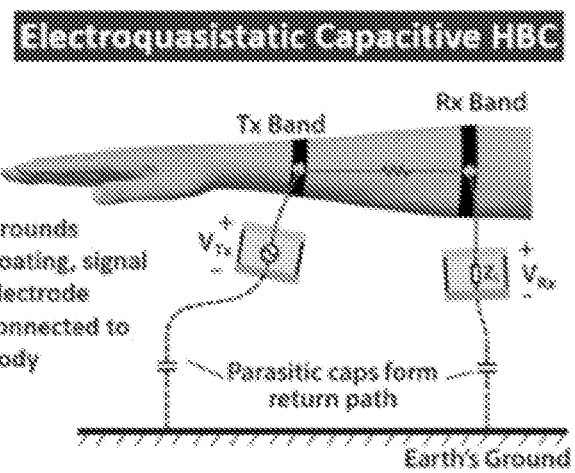
FIGS. 1A-D depict a comparison between Electro Quasistatic HBC and Magneto Quasistatic HBC.

It is to be understood that the following disclosure describes several exemplary embodiments for implementing different features, structures, or functions of the disclosure. Exemplary embodiments of components, arrangements, and configurations are described below to simplify the present disclosure; however, these exemplary embodiments are provided merely as examples and are not intended to limit the scope of the disclosure. Additionally, the present disclosure can repeat reference numerals and/or letters in the various embodiments and across the figures provided herein. This repetition is for the purpose of simplicity and clarity and does not in itself dictate a relationship between the various embodiments and/or configurations. Moreover, the exemplary embodiments presented below can be combined in any combination of ways, i.e., any element from one exemplary embodiment can be used in any other exemplary embodiment, without departing from the scope of the disclosure.

Additionally, certain terms are used throughout the following description and claims to refer to particular components. As one skilled in the art will appreciate, various entities can refer to the same component by different names, and as such, the naming convention for the elements described herein is not intended to limit the scope of the disclosure, unless otherwise specifically defined herein. Further, the naming convention used herein is not intended to distinguish between components that differ in name but not function.

Furthermore, in the following discussion and in the claims, the terms "including" and "comprising" are used in an open-ended fashion, and thus should be interpreted to mean "including, but not limited to." The phrase "consisting essentially of" means that the described/claimed composition does not include any other components that will materially alter its properties by any more than 5% of that property, and in any case does not include any other component to a level greater than 3 mass %.

The term "or" is intended to encompass both exclusive and inclusive cases, i.e., "A or B" is intended to be synonymous with "at least one of A and B," unless otherwise expressly specified herein.

The indefinite articles "a" and "an" refer to both singular forms (i.e., "one") and plural referents (i.e., one or more) unless the context clearly dictates otherwise. For example, embodiments using "an olefin" include embodiments where one, two, or more olefins are used, unless specified to the contrary or the context clearly indicates that only one olefin is used.

Unless otherwise indicated herein, all numerical values are "about" or "approximately" the indicated value, meaning the values take into account experimental error, machine tolerances and other variations that would be expected by a person having ordinary skill in the art. It should also be understood that the precise numerical values used in the specification and claims constitute specific embodiments. Efforts have been made to ensure the accuracy of the data in the examples. However, it should be understood that any measured data inherently contains a certain level of error due to the limitation of the technique and/or equipment used for making the measurement.

Each of the appended claims defines a separate invention, which for infringement purposes is recognized as including equivalents to the various elements or limitations specified in the claims. Depending on the context, all references to the "invention" may in some cases refer to certain specific embodiments only. In other cases, it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions, when the information in this disclosure is combined with publicly available information and technology.

Figure 1B:
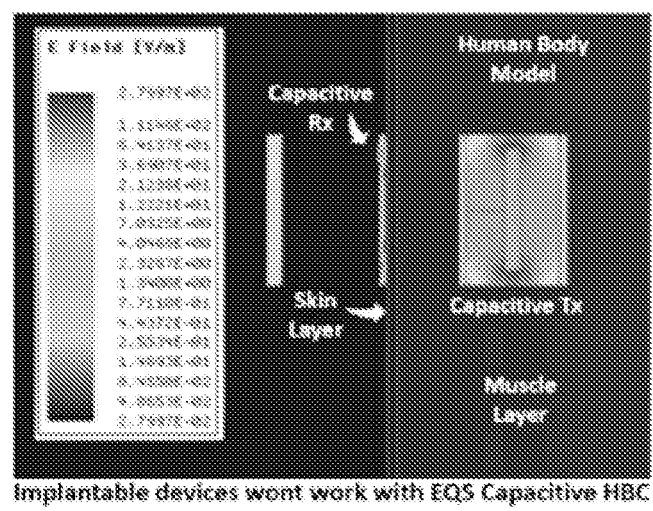
Figure 1C:
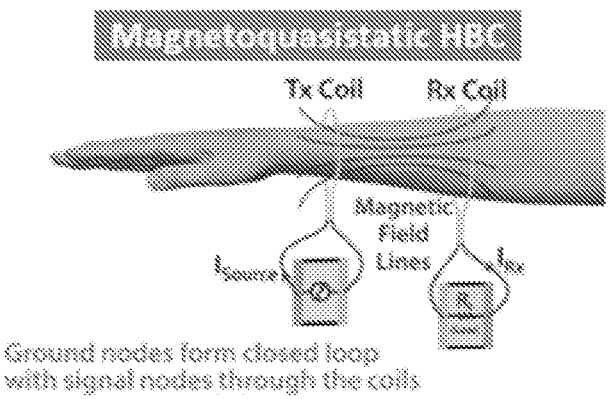

Remote communication between a controlling hub and a smart contact lens through traditional wireless body area network (WBAN) techniques operating in the radio frequency (RF) range, such as Bluetooth, is difficult—owing to the power consumption requirement of RF transceivers—making it hard to implement in a small form factor such as that of a contact lens. This necessitates the use of technologies that use lower power to operate, such as Human Body Communication (HBC). HBC uses the human body as a communication medium between multiple BAN devices. When operated in the quasistatic frequency range where the wavelength is large compared to the human body, HBC signals are confined within 5-15 cm of the body of the user, making it physically secure as well as power efficient compared to RF—as RF signals would be broadcasted farther away from the user, thus wasting energy and compromising security. A well-studied mode of quasistatic HBC for wearable BAN devices is capacitive Electro Quasi-Static HBC (EQS-HBC). EQS-HBC, as shown in FIG. 1A, uses the human body as a forward path between a Tx an Rx, while relies on parasitic capacitive coupling between earth's ground and the device's ground plane for the return path. The availability of this return path coupling to Earth's ground is critical in successful operation of an EQS-HBC device, and this unfortunately makes it unusable for implantable devices—where the implanted device's ground plate would be covered by the human body, without a direct coupling to earth's ground. This is demonstrated in FIG. 1B by simulating an implanted capacitive EQS device, showing minimal leakage of fields outside the body. Same would hold true for a smart contact lens, where the device can be considered partially implanted—the ground plate would be covered by the eyelid when the eye is closed, and even otherwise would show a very weak coupling to the earth, due to its very small ground plane area—thus making regular EQS HBC communication impractical. An alternative to EQS HBC has been recently shown as Magnetic HBC and MQS HBC, which due to the low tissue absorption of quasistatic magnetic field in the quasistatic frequency range will suite better for communicating with an implantable device. Wearable to wearable communication through magnetic HBC has been demonstrated for BAN devices.

A method for low-power and low-loss communication targeted towards wireless communication and powering between wearable and implantable Body Area Network (BAN) devices is described, which utilizes resonant Magneto Quasistatic (MQS) Human Body Communication (HBC). An application is described for communication between a smart necklace and a smart contact lens, where resonant MQS HBC is shown for the first time as a low power alternative to standard radio frequency (RF) wireless technology such as Bluetooth. The communication modality is frequency tunable by modifying a capacitance at the transmitter, as well as switchable between communication and powering mode by varying the source resistance. This simple manipulation of the source impedance provides a broad range of adaptability for implementing in BAN devices such as the demonstrated example of necklace and smart contact lenses, as well as any other pair of wearable-implantable devices e.g. a headband and smart contact lenses, a cap and smart contact lenses, a chest band and a pacemaker, a waist-belt and a stomach implant, a knee-cap and a knee-implant, a wrist band and a wrist implant etc.

In this disclosure, an improved HBC communication scheme can be described by using Resonant Magneto Quasistatic (R-MQS) HBC that can be used for both communication and powering between a wearable and an implantable device; and demonstrating low-loss communication between a smart contact lens (implant) and a smart necklace (wearable). The proposed R-MQS wearable to implantable communication mode demonstrates low channel loss compared to electro-quasistatic (EQS) HBC devices due to negligible absorption in the tissue in the quasistatic frequency range, tunable operating frequency, switch-ability between communication and powering mode by manipulating the transmitter resistance, high impedance receiver coil termination for communication mode and impedance matched receiver termination for power mode, possible low path loss (~50 dB) for frequencies 1 kHz-1 MHz, as well as 1 MHZ-20 MHz leading to a low loss power efficient high data rate communication.

Figure 2A:
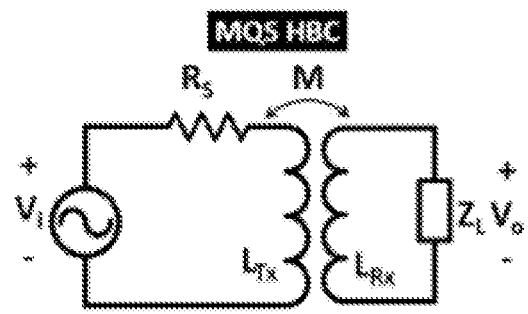
FIGS. 2A-B depict the basic circuit schematic for Magneto Quasistatic HBC.

FIG. 2A captures the basic circuit schematic for Magneto Quasistatic HBC (MQS HBC). A communication signal can be transmitted via a transmitting coil as an alternating magnetic field, which is captured as the potential induced in a coil across a load resistance. For a general source impedance $Z_S$ and a general load impedance $Z_L$, the voltage transfer ratio between the transmitter and receiver can be calculated by:

$$\frac{V_O}{V_I} = \frac{j\omega M Z_L}{(j\omega L_{TX} + Z_S)(j\omega L_{RX} + Z_L) + w^2 M^2}$$

Figure 2B:
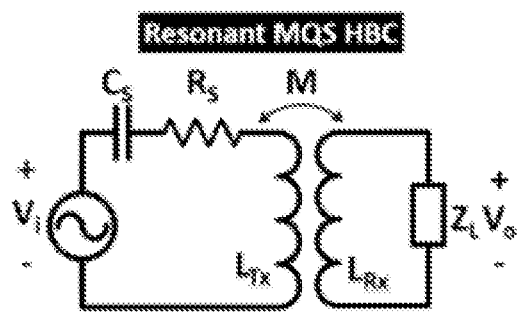

If a finite source resistance $R_S$ is used for the source resistance, this creates a voltage-transfer maximum in the MQS region, at the frequency, $f \approx R_S/2\pi L_{Tx}$. This creates a peak in the voltage-transfer vs frequency characteristics, that only depends on the source resistance. This can be modified however, if the inductance $L_{Tx}$ of the transmitter coil is resonated with a capacitor at a frequency of choice, as shown in the circuit in FIG. 2B. Adding the capacitor enables tunability of the peak frequency for signal transfer, as well as increases the over-all peak signal transfer at the resonating frequency.

Figure 1D:
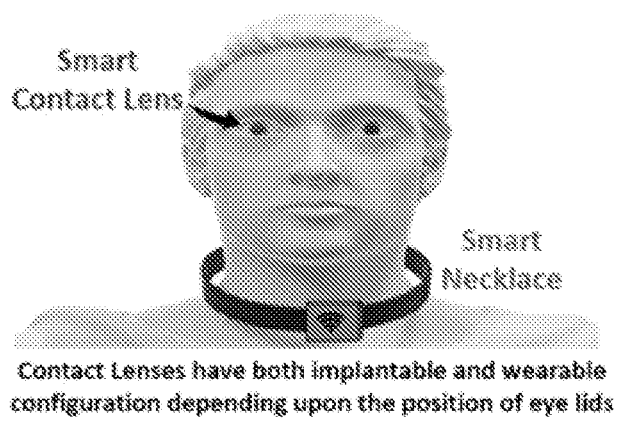
Figure 3:
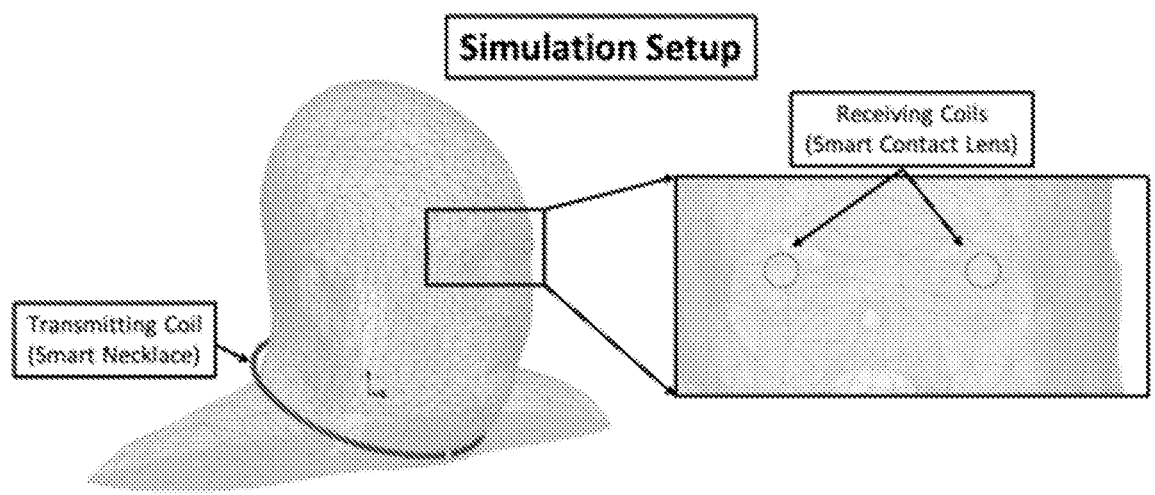
FIG. 3 depicts a simulation of an implementation of the Resonant MQS communication in Ansys HFSS, an FEM based electromagnetic solver.
Figure 4A:
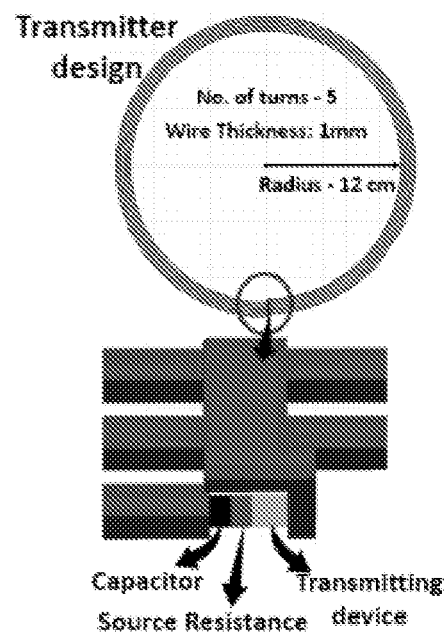
FIGS. 4A-D depict the results of a simulation of an implementation of the Resonant MQS communication in Ansys HFSS.
Figure 4B:
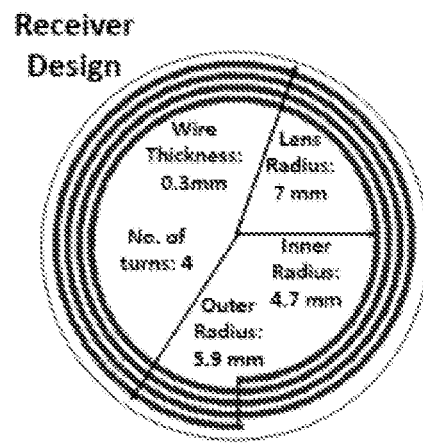
Figure 4C:
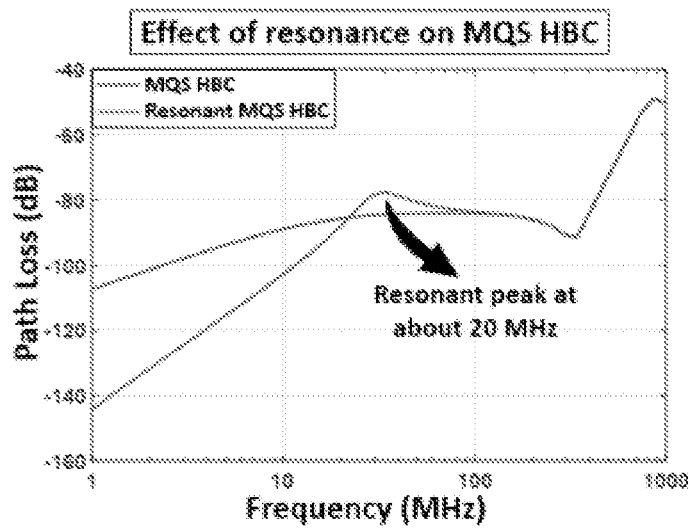
Figure 4D:
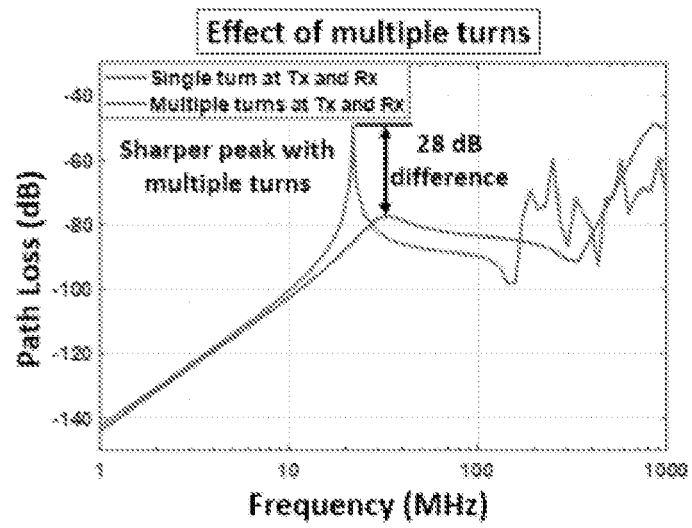

An implementation of the Resonant MQS communication can be realized for a smart contact lens as shown in FIG. 1D, with the transmitting device attached to a necklace that functions as the transmitting coil, whereas a receiving coil can be placed at the circumference of the contact lens. Different cases of this implementation are simulated in Ansys HFSS, an FEM based electromagnetic solver, using the simulation model shown in FIG. 3. The human head model can be adapted from VHP Female model available at NEVA EM, with human tissue properties taken from Gabriel database. The results are presented in FIG. 4. A necklace of diameter 12 cm can be assumed, and a receiver coil of average diameter 10 mm can be assumed at the smart contact lens. The transmitting coil can be excited with an AC source with a RS=25Ω. FIG. 4 C shows a comparison between a resonating and non-resonating transmitter cases, with both the receiver and transmitter coil consisting of only a single turn. The resonating transmitter shows a higher voltage transfer ratio peak, as described in the previous paragraph. Note that a high frequency peak id also seen near 1 GHz. This corresponds to a frequency range where the wavelength becomes comparable to the coil lengths making them efficient antennae, and hence the communication mode switches from MQS to RF. The RF mode would consume much higher power compared to the lower frequency MQS mode, making the MQS mode a better choice for communication. The transfer ratio can be further improved if the coils are made multi-turn and the resonating capacitor can be adjusted accordingly to account for the change in LTx. An optimal configuration can be demonstrated where the transmitting coil has 5 turns, and the receiving coil has 4 turns. The comparison between the voltage transfer cases between single turn and multi turn coils is shown in FIG. 4 D.

Figure 5:
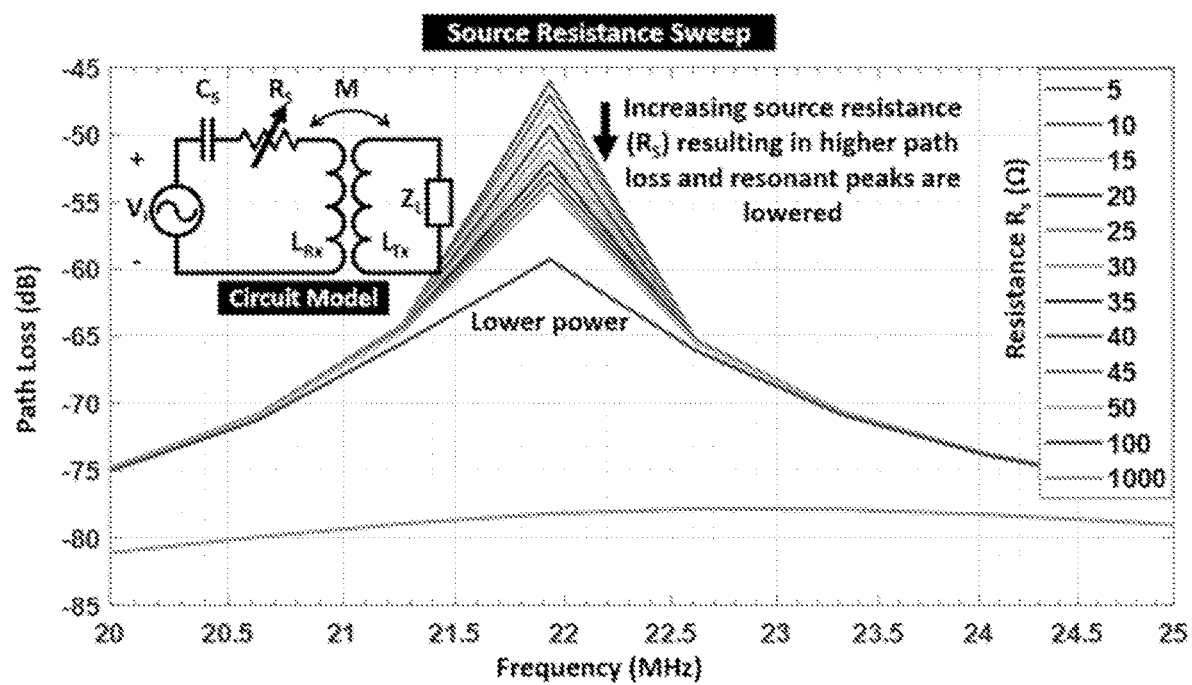
FIG. 5 depicts the flexibility of the transmitting mode by tuning the value of $R_S$.

Finally, FIG. 5 demonstrates the flexibility of the transmitting mode by tuning the value of RS. A low RS (eg 25Ω) would translate into a high Q sharp peak, and a low path loss (eg 50 dB). This would result into a relatively high-power consumption at the transmitter but enable wireless powering of the receiver through Resonant MQS powering. A high RS (eg 100Ω) would translate into a higher peak path loss (eg 59 dB), but would reduce the transmitter power consumption by a ratio of R¬S2. Thus, the proposed resonant MQS technology enables both wireless communication and powering between a wearable and an implantable device, while at the same time being energy efficient compared to RF based technologies, such as Bluetooth.

All patents and patent applications, test procedures (such as ASTM methods, UL methods, and the like), and other documents cited herein are fully incorporated by reference to the extent such disclosure is not inconsistent with this disclosure and for all jurisdictions in which such incorporation is permitted.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges appear in one or more claims below.

The foregoing has also outlined features of several embodiments so that those skilled in the art can better understand the present disclosure. Those skilled in the art should appreciate that they can readily use the present disclosure as a basis for designing or modifying other methods or devices for carrying out the same purposes and/or achieving the same advantages of the embodiments disclosed herein. Those skilled in the art should also realize that such equivalent constructions do not depart from the spirit and scope of the present disclosure, and that they can make various changes, substitutions, and alterations herein without departing from the spirit and scope of the present disclosure, and the scope thereof is determined by the claims that follow.

What is claimed is:

1. A communication and power system comprising:
   a wearable device comprising a transmitter coil having a variable transmission resistance, a first transmission impedance, and a second transmission impedance;
   an implanted device, comprising a receiver coil having a variable reception resistance, a first reception impedance, and a second reception impedance;
   wherein the transmitter coil of the wearable device can wirelessly transmit information over a variable frequency to the receiver coil of the implanted device when the variable resistance of the transmitter coil is tuned to the variable resistance of the receiver coil, the transmitter coil is configured to the first transmission impedance, and the receiver coil is configured to the first reception impedance;
   wherein the transmitter coil of the wearable device can wirelessly transmit power to the receiver coil of the implanted device when the transmitter coil is configured to the second transmission impedance and the receiver coil is configured to the second reception impedance; and
   wherein the transmitter coil of the wearable device can wirelessly transmit to the receiver coil of the implanted device using a magnetoquasistatic field.

2. The system of claim 1, wherein the wireless transmission occurs over a variable frequency between 1 kHz and 20 MHz.

3. The system of claim 1, wherein the transmitter coil has at least 5 turns and the receiving coil has at least 4 turns.

4. The system of claim 1, wherein the wearable device includes a necklace, headband, cap, or helmet and the implanted device includes a contact lens.

5. The system of claim 1, wherein the wearable device includes a chest band and the implanted device includes a pacemaker.

6. The system of claim 1, wherein the wearable device includes a waist band and the implanted device includes a stomach implant.

7. The system of claim 1, wherein the wearable device includes a knee wrap and the implanted device includes a knee implant.

8. The system of claim 1, wherein the wearable device includes a wrist band and the implanted device includes a wrist implant.

\* \* \* \* \*